US012569123B2

(12) United States Patent
Flanagan et al.

(10) Patent No.: US 12,569,123 B2
(45) Date of Patent: Mar. 10, 2026

(54) EXPANDABLE GUIDE DEVICES, SYSTEMS, AND METHODS

(71) Applicant: Boston Scientific Scimed, Inc., Maple Grove, MN (US)

(72) Inventors: Aiden Flanagan, County Galway (IE); Bryan Allen Clark, Forest Lake, MN (US); Daniel J. Foster, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 756 days.

(21) Appl. No.: 17/476,972

(22) Filed: Sep. 16, 2021

(65) Prior Publication Data

US 2022/0095901 A1     Mar. 31, 2022

Related U.S. Application Data

(60) Provisional application No. 63/083,961, filed on Sep. 27, 2020.

(51) Int. Cl.
*A61B 1/018*      (2006.01)
*A61B 1/00*      (2006.01)
(Continued)

(52) U.S. Cl.
CPC .......... *A61B 1/018* (2013.01); *A61B 1/00082* (2013.01); *A61B 1/01* (2013.01); *A61B 1/31* (2013.01)

(58) Field of Classification Search
CPC ....... A61B 1/018; A61B 1/00082; A61B 1/01; A61B 1/31; A61B 1/00148; A61B 1/00154; A61B 5/6853; A61B 2017/3486; A61B 17/3421; A61B 1/00135; A61B 2018/0022; A61B 2017/00557; A61B 17/3423; A61B 17/12136; A61B 17/0218; (Continued)

(56) References Cited

U.S. PATENT DOCUMENTS 8,187,173 B2     5/2012 Miyoshi
9,596,979 B2     3/2017 Terliuc et al.
(Continued)

FOREIGN PATENT DOCUMENTS

JP          2007521907 A      8/2007

OTHER PUBLICATIONS

Meseeha et al; "Endoscopic Retrograde Cholangiopancreatography," In: StatPearls [Internet]. Treasure Island (FL): StatPearls Publishing; Jan. 2022, [Updated Aug. 11, 2021.].

*Primary Examiner* — Tan-Uyen T Ho
*Assistant Examiner* — Bridget E. Rabaglia
(74) *Attorney, Agent, or Firm* — Seager, Tufte & Wickhem LLP

(57)          ABSTRACT

The present disclosure, in its various aspects, is directed to expandable guide devices, implementation methods, and related delivery systems. Embodiments according to the present disclosure, including as described herein, may increase the effectiveness and efficiency of endoscopy procedures. In one example, an expandable guide device is configured to receive an instrument through an instrument lumen of the device, wherein the device comprises first and second bodies, with first and second expandable members disposed about the first and second bodies.

18 Claims, 12 Drawing Sheets

(51) Int. Cl.
    *A61B 1/01*        (2006.01)
    *A61B 1/31*        (2006.01)
(58) Field of Classification Search
     CPC .... A61B 2017/3492; A61B 2018/0212; A61B
            17/00234; A61B 17/12022; A61B 1/0676;
            A61B 1/005; A61B 2018/00285; A61M
            2025/1015; A61M 2025/09008; A61M
            25/1011; A61M 25/1002; A61M 25/10;
            A61M 29/02; A61M 25/04; A61M
            2025/1052; A61M 2025/105; A61M
            2025/1093; A61M 25/1018; A61M
            2025/109; A61M 2025/0681; A61M
            25/10184; A61M 2025/09125; A61M
            25/0662; A61M 2025/1013; A61M
            25/1006; A61M 25/0026; A61M
            2025/1068; A61M 2025/1075; A61M
            25/0074; A61M 2025/0293; A61M
            2025/1072; A61M 2025/1004; A61M
                                        2025/1047
     See application file for complete search history.

(56)                References Cited

U.S. PATENT DOCUMENTS

| | | | |
|---|---|---|---|
| 2005/0245788 A1 | 11/2005 | Gerber | |
| 2007/0244361 A1* | 10/2007 | Ikeda | A61B 1/12 |
| | | | 600/116 |
| 2008/0064930 A1* | 3/2008 | Turliuc | A61B 1/00154 |
| | | | 600/156 |
| 2008/0249358 A1 | 10/2008 | Motai et al. | |
| 2011/0118546 A1 | 5/2011 | Dillon et al. | |
| 2011/0190583 A1 | 8/2011 | Ashida et al. | |
| 2014/0171914 A1* | 6/2014 | Rowe | A61M 25/09 |
| | | | 604/528 |
| 2015/0150436 A1* | 6/2015 | Cornhill | A61M 25/1018 |
| | | | 600/115 |
| 2020/0146530 A1 | 5/2020 | Cruz et al. | |

* cited by examiner

134

130

140

136

122

170

150

120

116

120

140

114

110

112

100

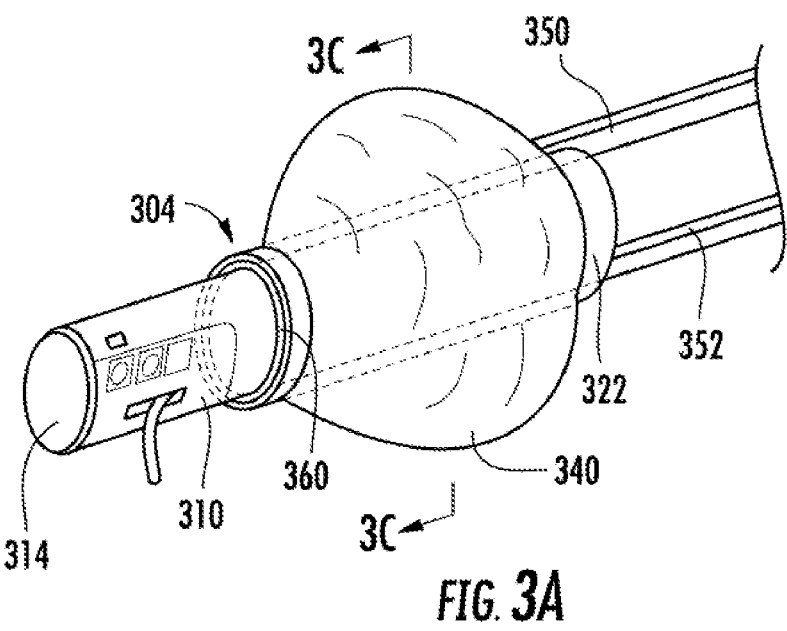
FIG. 3A
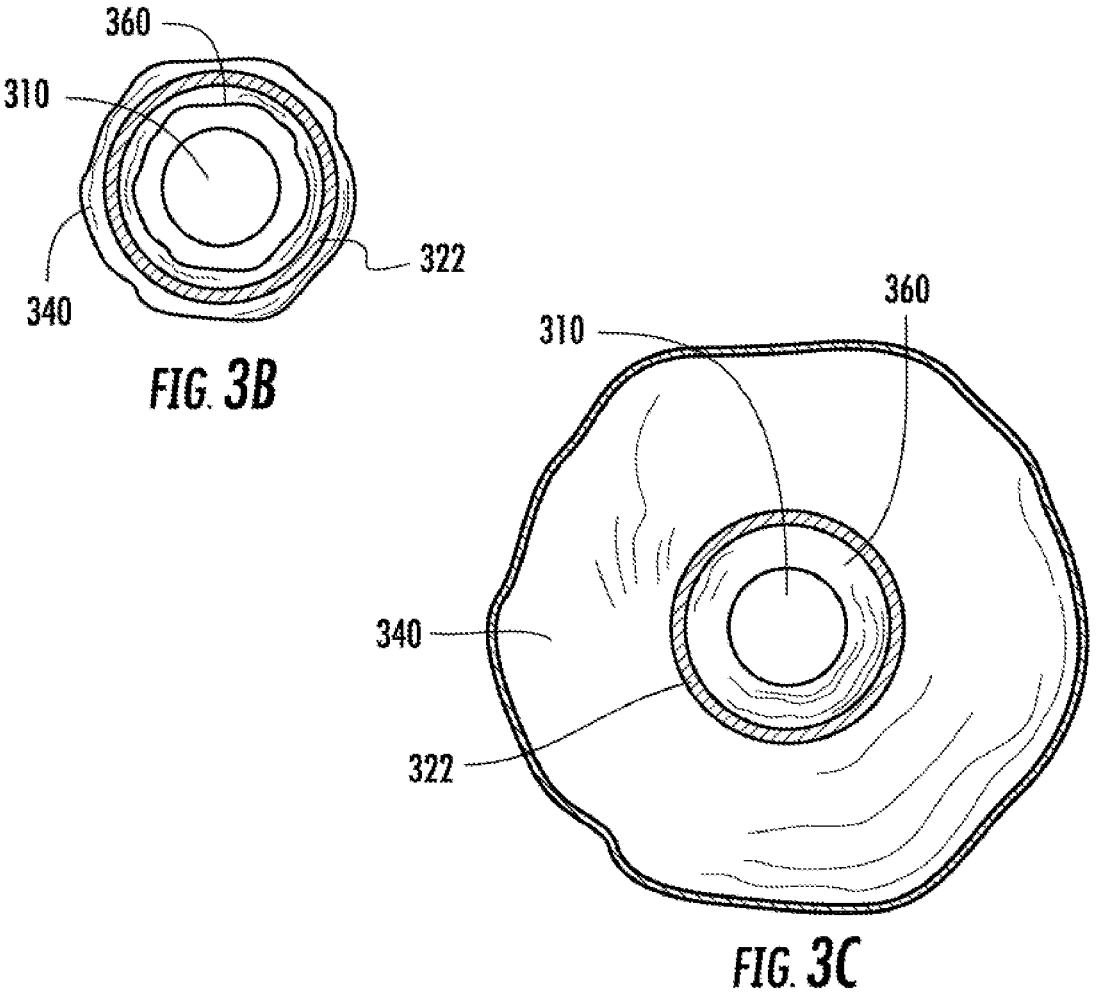
FIG. 3B
FIG. 3C

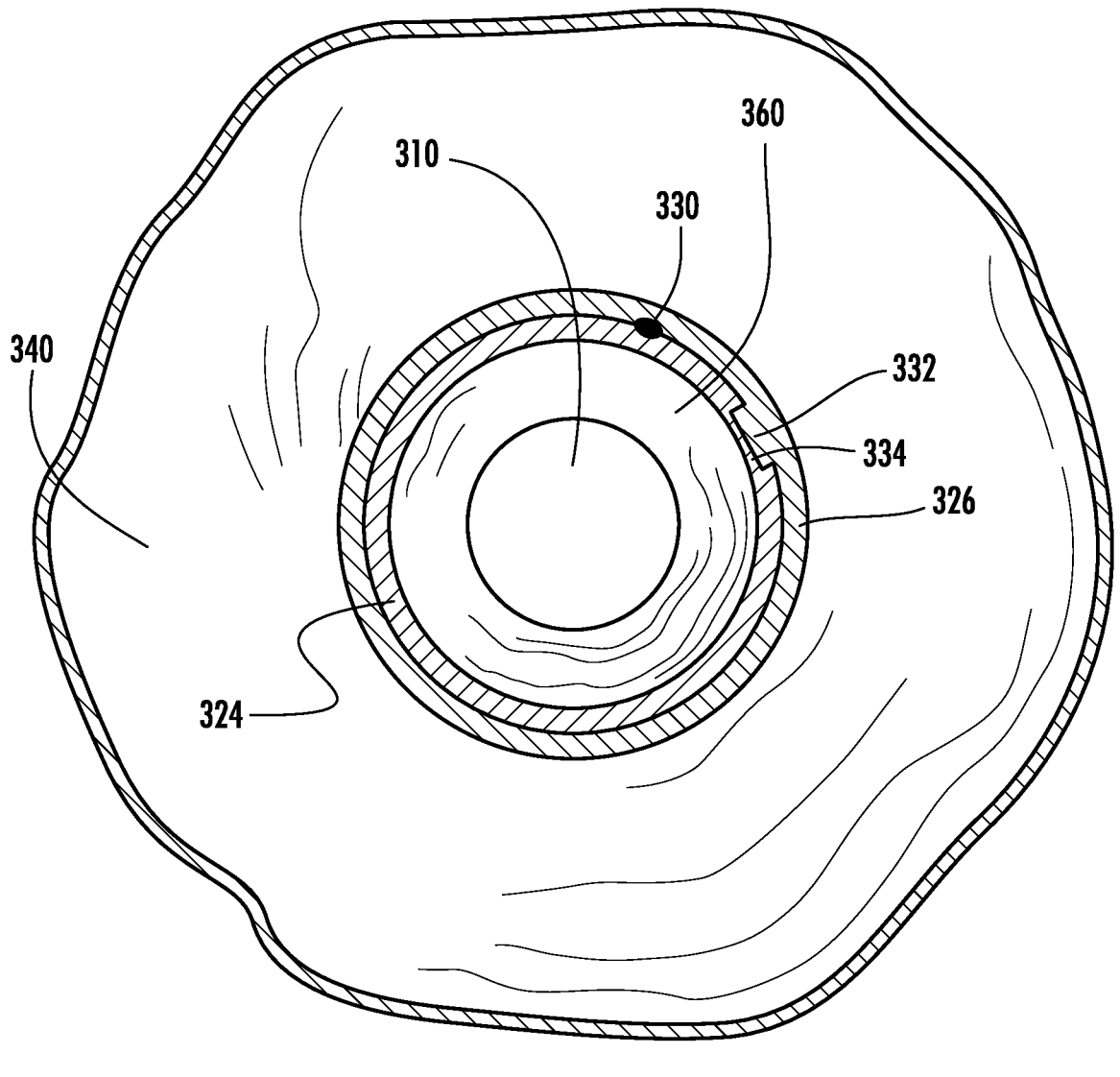
*FIG.* 3G

EXPANDABLE GUIDE DEVICES, SYSTEMS, AND METHODS

PRIORITY

The present application is a non-provisional of and claims the benefit of priority under 35 USC § 119 to, U.S. Provisional Application Ser. No. 63/083,961, filed Sep. 27, 2020, which is incorporated by reference herein in its entirety and for all purposes.

FIELD

The present disclosure pertains to medical devices. More particularly, the present disclosure pertains to expandable guide devices and related systems and methods, specifically as may increase the effectiveness and efficiency of endoscopic procedures.

BACKGROUND

Endoscopes, for example, are used in medical procedures to examine and treat conditions within the digestive tract. ERCP procedures are used to examine and treat issues in the common bile duct and pancreatic ducts. In some procedures, cannulation of the bile duct can be difficult, with movement in the duodenum making positioning and stabilization of the endoscope challenging to achieve. Further, the tightly contracted musculature of the duodenal papilla requires high levels of precision to maneuver through the papilla opening. Consequently, the effectiveness and efficiency of the procedure may become compromised, and the difficulty to cannulate the common bile duct may result in multiple or failed attempts.

It is with the above considerations in mind that the improvements of the present disclosure may be useful.

SUMMARY

The present disclosure, in its various aspects, is directed generally to expandable guide devices, implementation methods, and related systems. Embodiments according to the present disclosure, including those described herein, may increase particularly the effectiveness and efficiency of procedures used for the examination and treatment of conditions within the body, e.g., cannulation of the bile duct during ERCP.

In an aspect, embodiments of the disclosure describe an expandable guide device that may comprise a first body having a proximal end, a distal end, and an instrument lumen extending therethrough along a longitudinal axis. The instrument lumen may be configured to slidingly receive a first length of an instrument extendible therethrough. The first body may be configured to resist deformation. A first expandable member may be disposed about the first body. A second body may have a proximal end, a distal end, and an instrument lumen extending therethrough along a longitudinal axis. The instrument lumen may be configured to slidingly receive a second length of the instrument extendible therethrough, and a second expandable member may be disposed about the second body.

In various embodiments described herein and otherwise within the scope of the disclosure, the first and second expandable members may comprise a compliant expandable material. The device may further comprise at least one delivery member in fluid communication with at least one of the first and second expandable members. The at least one delivery member may be in fluid communication with both the first and second expandable members. The at least one delivery member may be in fluid communication with a supply of $CO_2$, contrast fluid, shear-thinning material, or air. The second body may comprise a compliant expandable material. The instrument lumen of the second body may be configured to be frictionally contacted with the instrument. The first expandable member may comprise a plurality of chambers. Each chamber of the plurality of chambers may comprises an independent delivery member of the at least one delivery member and each chamber may be independently expandable with respect to the other chambers of the plurality of chambers. The first expandable member may further comprise a sensor. A central axis of the first body may be offset from a central axis of the first expandable member when the first expandable member is in an expanded configuration. The first body may comprise the first expandable member disposed about an outer surface of the first body and a third expandable member disposed about an inner surface of the first body. An inner surface of the first body may further comprise a lubricious coating. The at least one delivery member may be in fluid communication with the first expandable member and the second expandable member. The distance between the first body and second body may be fixed. The device may further comprise an elongate member disposed along an outer surface of the first body, the elongate member comprising a second lumen extending therethrough. The first expandable member, or second expandable member, or both, may be spherical-shaped, oblong-shaped, or ellipsoidal-shaped.

In an aspect, embodiments of the disclosure describe a system that may comprise an instrument and an expandable guide device. The device may be slidingly disposed about the instrument and may comprise a body having a proximal end and a distal end. The body may be configured to resist deformation. The first expandable member may be disposed about an outer surface of the body. A second expandable member may be disposed about an inner surface of the body. The second expandable member may define an instrument lumen where the instrument lumen may extend through the body along a longitudinal axis. The instrument may be configured to slidingly receive a length of the instrument extendible therethrough.

In various embodiments described herein and otherwise within the scope of the disclosure, the first expandable member and the second expandable member may be configured to be expanded independently of each other.

In an aspect, embodiments of the disclosure describe a method that may comprise coupling an expandable guide device with an instrument. The device may include a first expandable member and a second expandable member. The method may comprise inserting the instrument and device into a body lumen and advancing the instrument and device toward a treatment site. The method may further comprise expanding the first expandable member against a wall of the body lumen.

In various embodiments described herein and otherwise within the scope of the disclosure, expanding the first expandable member may allow for longitudinal and rotational movement of the instrument relative to the expandable guide device. The method may further comprise expanding the second expandable member to provide lateral stabilization of the instrument with respect to the body lumen. The first expandable member may be expanded to place the instrument in position to interact with the treatment site, and the second expandable member may be expanded to laterally stabilize the instrument with respect to the body lumen.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures:

FIG. 3A illustrates a perspective view of an expandable guide device in an expanded configuration, in accordance with an embodiment of the present disclosure.

FIG. 3B illustrates a cross-sectional view of the expandable guide device of FIG. 3A in an unexpanded configuration.

FIG. 3C illustrates a cross sectional view of the device of FIG. 3A.

FIG. 3G illustrates a cross sectional view of an expandable guide device in a locked configuration, in accordance with an embodiment of the present disclosure.

DETAILED DESCRIPTION

Figure 1A:
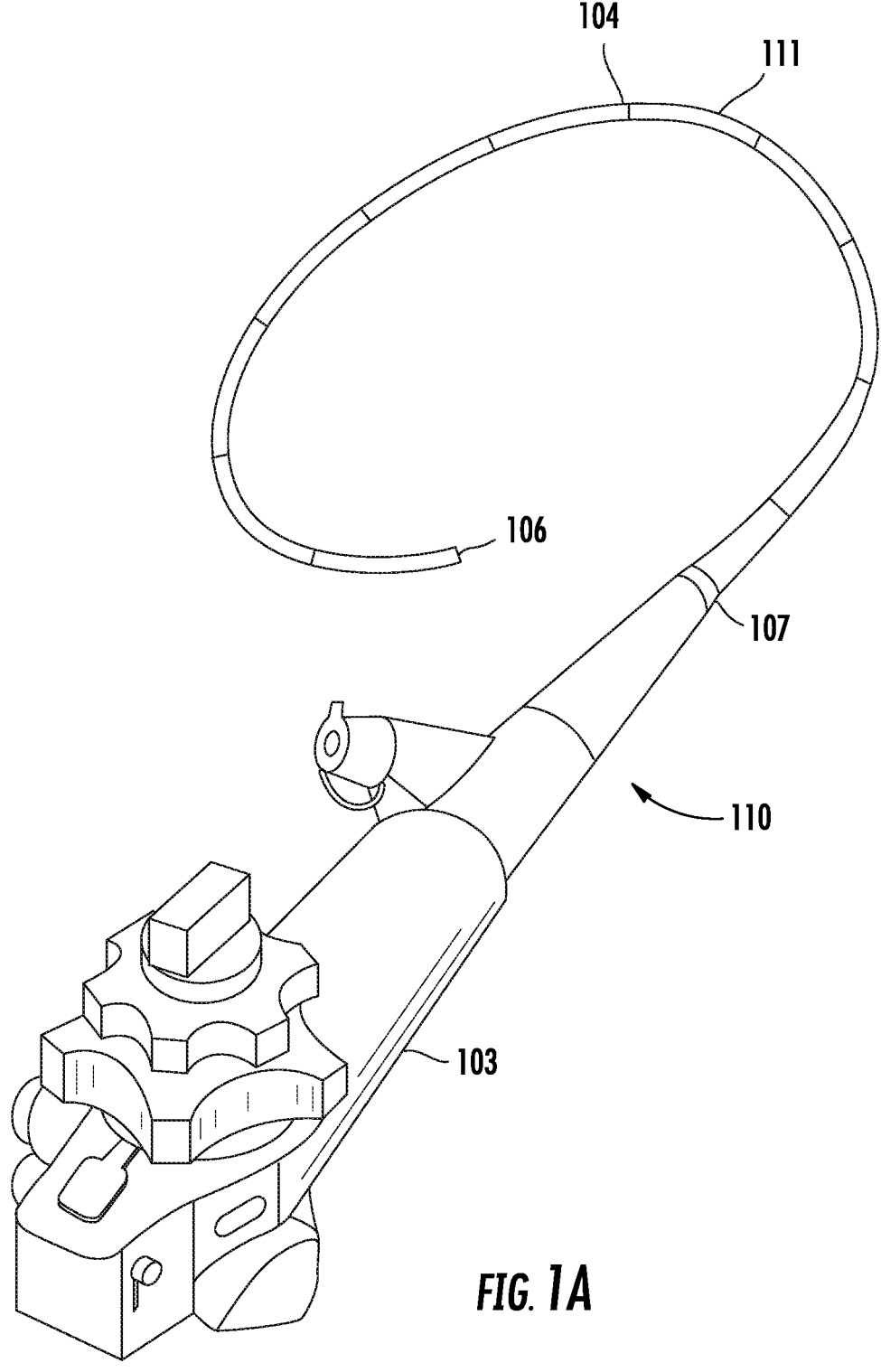
FIG. 1A illustrates an exemplary instrument of a type described in embodiments of the present disclosure.

It is the case, generally, that with any form of endoscopy or other procedure where any other instrument is inserted in the body it may be important to be able to stabilize the instrument in place once it is navigated to a desired position, to locate the instrument in a particular radial position defined by a cross-section of the body lumen, to orient an instrument in a particular manner dictated by a specific procedure, and the like.

Various embodiments according to the present disclosure are described below. As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The detailed description should be read with reference to the drawings, which are not necessarily to scale, depict illustrative embodiments and are not intended to limit the scope of the invention.

Embodiments of the present disclosure may include an expandable guide as a device for use with an instrument. An instrument may be an endoscope, duodenoscope, colonoscope, bronchoscope, gastroscope, ureteroscope, a catheter, tubing, or the like. The device may include various components and configurations. Embodiments of this disclosure may comprise a system. A system may include an instrument, an expandable guide device, a handle which extends to the expandable guide device and/or a source of inflation fluid, or the like. Embodiments of the devices and systems may be used to substantially fill a body lumen around the instrument, during an endoscopy, to enable the operator to stabilize or position the instrument within the body lumen. Various embodiments described herein comprise an expandable guide device having at least one expandable member about a body forming an instrument lumen which can slidingly receive a length of an instrument extendible therethrough. The expandable member once expanded within the body lumen may inhibit one or more of lateral, rotational, or translational movement of the instrument within the body lumen. In some embodiments, an expandable member may comprise an inflatable balloon, and the inflation fluid may be fluid, such as a gas, a liquid, or both. In some embodiments, the body lumen may include a lumen, organ, vessel, passage, or the like, within, e.g., the digestive system, or the like. In various embodiments, the distal end of the instrument may or may not extend past the distal end of the expandable guide device. In various embodiments, an expandable member may expand to a greater or lesser degree, may assume a different shape, and/or may exhibit different other properties than another expandable member. In various embodiments, the expandable guide device may be disposable. In alternate embodiments, the expandable guide device may be reusable.

ERCP is used to access, examine and treat issues in the common bile duct and pancreatic ducts. An endoscope may be introduced into the patient, e.g., via the mouth, through the stomach and advanced through at least a portion of small intestine. The endoscope may be used to access the ampulla or papilla of Vater in order to reach the pancreatic and bile ducts. The positioning and/or angle of approach of the endoscope relative to the duodenal papilla may be important to the success of the procedure, and may be made difficult by movement and breathing of the patient, movement of the duodenum, and/or operation of tools within or in relation to the endoscope. In order for a user to perform ERCP, the distal end of an instrument must be sufficiently stabilized within the body lumen at the ampulla or papilla of Vater, which requires extreme precision. Once placed in position, the instrument (e.g., endoscope) needs to be kept stable enough to facilitate access to and entry into and through the ampulla or papilla of Vater by the instrument and/or by an accessory device (e.g., biopsy tool) delivered through a working channel of the instrument and/or the expandable guide device.

A number of medical procedures, including intravascular procedures, procedures along the digestive, urinary, respiratory, reproductive and/or biliary tracts, thoracic and pulmonary procedures, etc., utilize instruments, such as endoscopes, to access tissue intended for diagnosis or treatment (e.g., "target tissue") within the body. In some instances, an endoscope may incorporate features which assist the physician in visualizing and performing a treatment on the tissue. For example, some endoscopes may include a light and/or camera designed to illuminate and/or visualize the body lumen as the endoscope is navigated and positioned adjacent to a target tissue site. Additionally, some endoscopes may also include a lumen (e.g., a working channel) through which a resecting device, grasping member, or other accessory devices may be deployed and utilized. Additional visualization and/or external and/or internal imaging methods may be alternatively or additionally employed, e.g., fluoroscopy.

Exemplary devices, systems, and methods with which embodiments of the present disclosure may be implemented include, but are not limited to, those described in the complete disclosures of U.S. Provisional Patent Application No. 63/071,125, titled Devices, Systems, and Methods for Pyloric Occlusion, filed Au. 27, 2020; U.S. Provisional Patent Application No. 63/071,412, titled Stabilization and Leverage Devices, Systems, and Methods, filed Aug. 28, 2020; U.S. Provisional Patent Application No. 63/083,960, titled Expandable Guide Devices, Systems, and Methods, filed even date herewith; and U.S. Provisional Patent Application No. 63/083,962, titled Expandable Guide Devices, Systems, and Methods, filed even date herewith, each of which disclosures are herein incorporated by reference in their entirety.

Figure 1B:
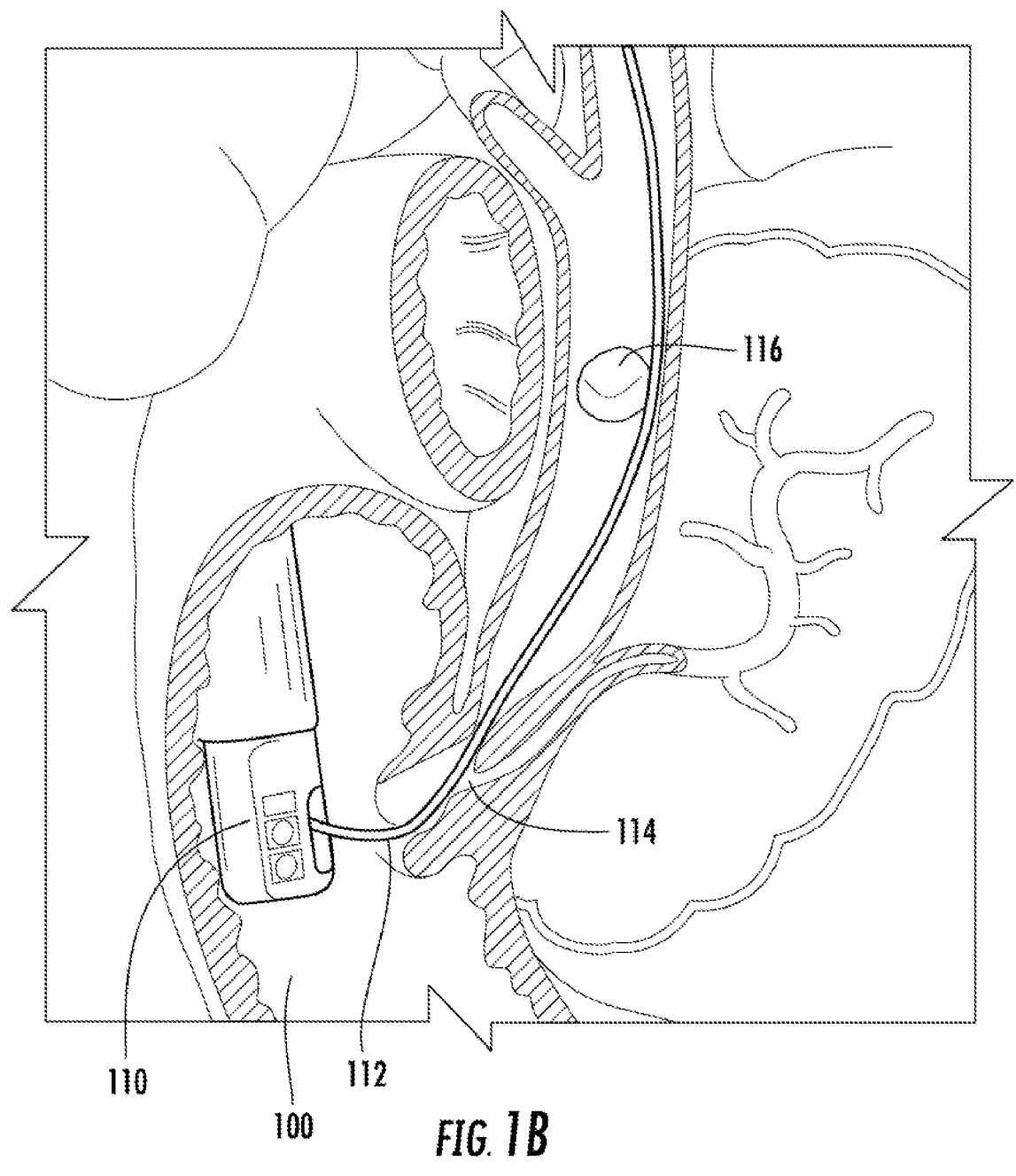
FIG. 1B illustrates a partial cross-sectional view of an endoscope within a body.

Referring to FIG. 1A, an embodiment of an instrument is illustrated, which may be used with an expandable guide device as described herein. The instrument 110 e.g., an endoscope, comprises a distal end 106 and a proximal end 107 with a lumen or working channel extending therethrough. A handle 103 at the proximal end 107 may be operated by a medical professional to manipulate the instrument 110. The instrument 110 may include cuts or channels 104 along a wall 111 of the insertion portion (e.g., flexible tubing) of the instrument 110 in order to facilitate movement and flexibility of the instrument 110 within a patient, e.g., by operation of steering knobs at the handle 103. FIG. 1B depicts the instrument 110 (e.g., a duodenoscope) within a body lumen 100 (e.g., the duodenum). In this depiction, a catheter 112 extends out from the instrument 110 and through a papilla of Vater 114 in order to dislodge an obstruction 116 shown within the biliary duct.

As used herein to describe the various embodiments described herein or otherwise within the scope of the disclosure, an inner surface of a body refers to a surface facing the instrument lumen and instrument when received therein. An outer surface of a body refers to a surface facing the body lumen.

Figures 1C, 1D:
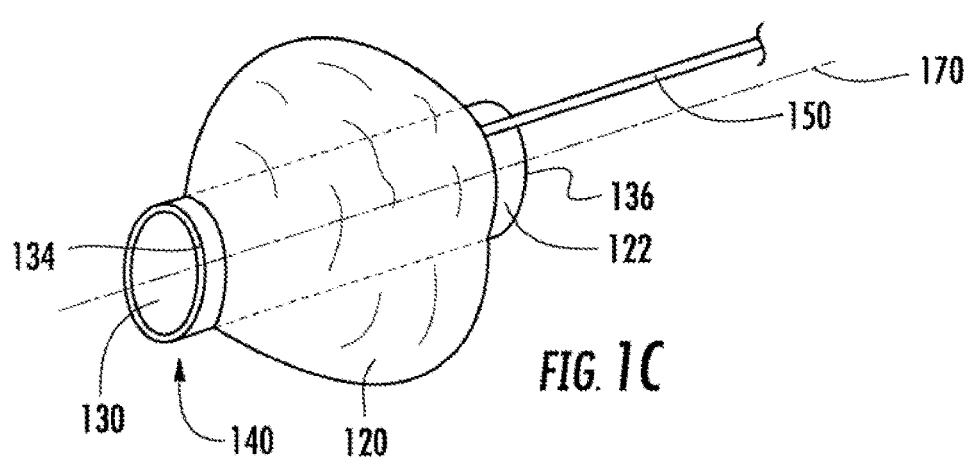
FIG. 1C illustrates an exemplary expandable guide device in an expanded configuration, according to an embodiment of the present disclosure.
FIG. 1D illustrates a partial cross-sectional view of an endoscope system with the expandable guide device of FIG. 1C in an expanded configuration, according to an embodiment of the present disclosure.

Examples of expandable guide devices for use with instruments, such as the endoscope of FIGS. 1A-1B, are described. FIG. 1C illustrates an expandable guide device 140 according to an embodiment of the present disclosure. The device 140 includes a first expandable member 120 disposed about a first cylindrical body 122. The expandable member 120 is illustrated in an expanded configuration. The expandable member 120 extends from a distal end 134 of the body 122 to the proximal end 136 along a longitudinal axis 170. The body 122 comprises an instrument lumen 130 extending therethrough between the distal end 134 and the proximal end 136. A delivery member 150 is in fluid communication with the expandable member 120 and extends proximally away from the body 122. A lubricious coating (e.g., KY Jelly, silicone oil, Teflon, adhered hydrophilic coatings (e.g., ZGlide™), a combination thereof, and the like) may be applied along the inner surface of the body 122 to improve axial movement of an instrument within the instrument lumen 130. The inner surface of the body 122 could alternatively or additionally be an arrangement of ball bearings or roller bearings to accomplish a similar purpose as the hydrophilic coatings. Further, a positive pressure of seeping fluid on or between surfaces could be used to create a frictionless cushion. Also, contact area minimization structures could be used such as ridges or bumps on the surfaces.

FIG. 1D illustrates the device 140 of FIG. 1C disposed about the instrument 110 in the expanded configuration within the body lumen 100. The expandable member 120 is expanded against the wall of the body lumen 100, thereby assisting with stability of the instrument 110. Stability is achieved compared to the surrounding anatomy allowing for more efficient and stable operation of the catheter 112 within the papilla 114 and accessing the obstruction 116. The expandable member 120 facilitates axial and rotational movement of the instrument 110 within the body of the device, and substantially prevents radial or lateral movement within the body lumen 100.

In various embodiments described herein or otherwise within the scope of the disclosure, an expandable guide device may include an expandable member. An expandable guide device may include one or more expandable members that may be an internal expandable member and/or an external expandable member. The expandable members may be segmented or chambered and each segment or chamber may be independently expandable, e.g., to affect different shapes of the expandable member around the circumference of the device by maintaining unexpanded, or partially expanding, or expanding, various of the chambers of the expandable member. An expandable member may comprise a compliant expandable material such a silicone, latex, rubber, polyurethane, a combination thereof, or the like. An expandable member may be mechanically actuated, electrically actuated, pneumatically actuated, inflated, or the like. An expandable member may transition from an unexpanded configuration to an expanded configuration (including a partially expanded configuration) to occlude, stretch, establish patency, or maintain patency of a body lumen. An expandable member may be used to center or position the instrument within the body lumen. An expandable member may be used to manipulate tissue of a body lumen for viewing or operation. An expandable member may be compliant or non-compliant, and may be spherical-shaped, oblong-shaped, or ellipsoidal-shaped. An embodiment may include a plurality of expandable members arranged around a single body. In an embodiment with a plurality of expandable members, each member may be independently expanded. An expandable member that is external to the body of the device may be used to stabilize the instrument within the body lumen, inhibit radial movement of the instrument, and/or prevent translational and axial movement of the instrument within the body of the device. An expandable member that is internal to the body of the device may be used to grip the instrument such that any movement of the instrument moves the expandable guide device together with the instrument.

An expandable member or other portions of the device may comprise one or more radiopaque markers at various positions about and along the device. The radiopaque marker may be imaged during a procedure allowing for, e.g., the position of the device or devices with respect to each other, with respect to the instrument, and/or with respect to a portion of the body lumen, to be determined, changed, confirmed, etc., and the like. The degree of expansion of the expandable members may be confirmed as well. Also, contrast fluid that is imageable may be injected in the body lumen, or the inflation fluid for the expandable members may be made radiopaque. Radiopaque markers may include radiopaque filler compounded into the material of the expandable member and/or independent markers may be affixed to the interior or exterior of the expandable members, to the surfaces of the body, or to other portions of the device.

In various embodiments described herein or otherwise within the scope of the disclosure, an expandable guide device may include a body. A body may have a proximal end and a distal end. A body may be a flexible but not expandable material such as LDPE, HDPE, Pebax, nylon, PEEK, PTFE, metal (stainless steel, NiTi, metal mesh, or the like) a combination thereof, or the like. The body may resist deformation due to the relative inelastic nature of the material of the body compared to the expanding surfaces of the expandable members. The body may be a sheath and may not add significant thickness to the instrument. The body may form an instrument lumen. The inner surface of the body may have frictional contact with an instrument while the instrument is in the instrument lumen. An inner surface of a body may include a lubricious coating along the instrument lumen. The body may have an elongate member as a sheath that extends the length of a tool or another instrument, which may be insertable along the elongate member. The elongate member may be attached along the length of the body from the proximal end of the body to the distal end of the body, on the inner or outer surface of the body or between the surfaces of the body. If the body runs the length of the accessory device, then the elongate member may be attached along the entire length of the device. If the body is shorter and is disposed at the distal end of the instrument, then the elongate member may be attached along the body or the bodies and may otherwise extend free of the expandable guide device along the outer surface of the instrument. The elongate member may include a lumen therethrough that may be configured to slidingly accept a tool, e.g., as an accessory to the instrument within the instrument lumen of the body, and/or as an accessory to another tool passed through a working channel of the instrument (e.g., endoscope working channel).

In various embodiments described herein or otherwise within the scope of the disclosure, an expandable member of an expandable guide device may have a fluid inlet that may extend through the outer surface of the expandable member. The fluid inlet may provide a fluid pathway to supply and/or return an inflation fluid for expanding and/or un-expanding the expandable member, e.g., in cases where the expandable member may be a balloon. Each expandable member may have its own independent or a shared fluid inlet and corresponding delivery member. At least one delivery member may extend along the outside of the instrument, to the proximal end of the instrument. Each expandable member may have an individual delivery member, or one delivery member may extend to multiple expandable members. The delivery members may run along the instrument in a single conduit. Alternatively, the body may be a sheath that extends the length of the instrument, with the delivery members embedded in the sheath. In an embodiment with a plurality of expandable members, one delivery member may be used to deliver fluid to the plurality of expandable members. The delivery members may also, or independently, be embedded within the body. The at least one delivery member may be in fluid communication with a supply of $CO_2$, contrast fluid, or air.

Figure 1E:
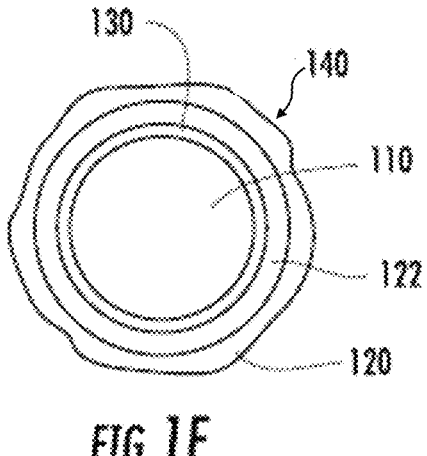
FIG. 1E illustrates a cross-sectional view of the expandable guide device of FIGS. 1C and 1D in an unexpanded configuration.
Figure 1F:
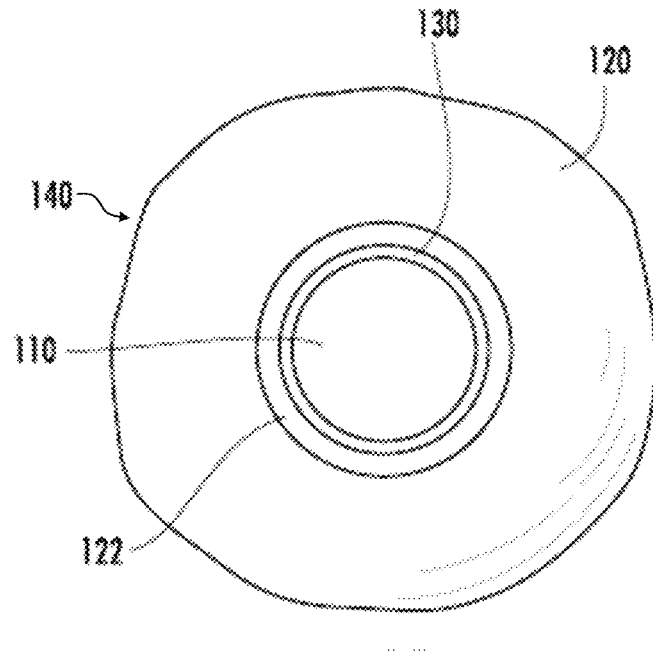
FIG. 1F illustrates a cross-sectional view of an expandable guide device of FIGS. 1C-1E in an expanded configuration.

FIGS. 1E and 1F illustrate cross sectional views of the expandable guide device 140 of FIGS. 1C and 1D slidably disposed about the instrument 110. In FIG. 1E, the expandable member 120 is in an unexpanded configuration about the body 122. The instrument 110 is slidably disposed within the instrument lumen 130 of the body 122. FIG. 1F illustrates the expandable member 120 in an expanded configuration about the body 122. The compliant expandable member 120 expands to fill the body lumen, while the instrument 110 is slidably disposed within the instrument lumen 130. The expandable guide device 140, when expanded, facilitates axial and rotational movement of the instrument but not radial. This allows the user to control the positioning and/or angle of approach of the instrument with greater precision during procedures, such as a cannulation procedures and reduces the chance of losing positioning and maintaining stability when performing exchanges and procedures.

In various embodiments described herein and otherwise within the scope of the disclosure, a stylet may also extend from a handle portion of the guide device, e.g., kept at the proximal end of the instrument, through an actuating member or delivery member of the device. The stylet can be used to push and/or pull the device in tandem with the instrument or relative to the instrument in order to position or reposition the device along and about the surface of the instrument. The stylet holds the device in place while only the instrument is moved relative to the device, or vice versa. When moving the device with the stylet relative to the instrument or moving the guide device and the instrument in tandem, the expandable member can be partially expanded or unexpanded. The movement of the device along and about the instrument can be in a distal or proximal direction. Alternatively, the expandable member is expanded and the stylet may be used to keep the device in place, allowing the instrument to be moved through the body lumen while the expanded expandable member keeps the body lumen stabilized. An expandable member may be expanded in order to contact the body lumen, partially expanded when the user is positioning the device and does not want to unexpand the expandable member, and unexpanded when moving the device through the body lumen.

Figures 2A, 2B, 2C:
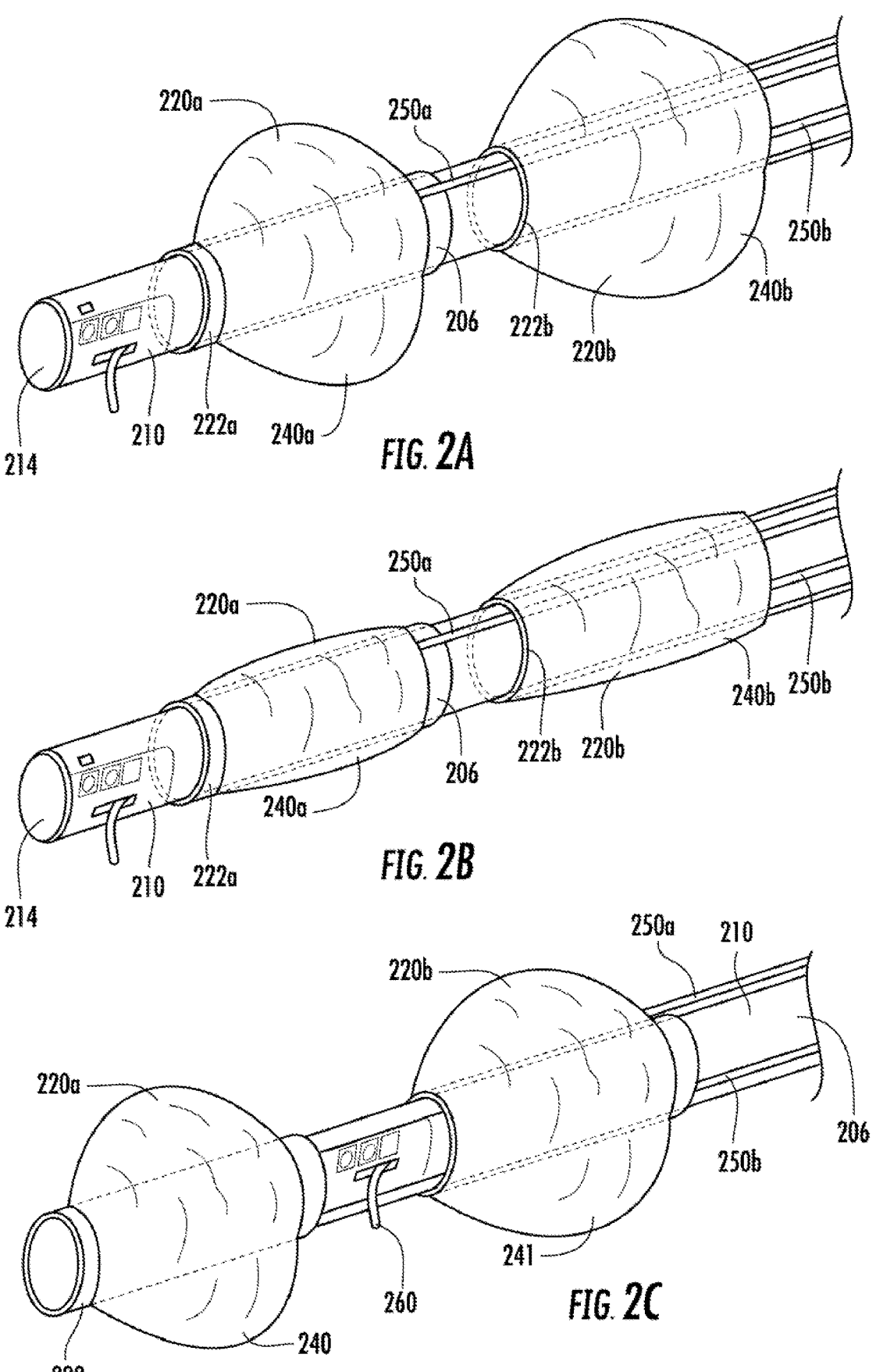
FIG. 2A illustrates a perspective view of an expandable guide device in an expanded configuration, in accordance with an embodiment of the present disclosure.
FIG. 2B illustrates a perspective view of the expandable guide device of FIG. 2A in an unexpanded configuration.
FIG. 2C illustrates a perspective view of an expandable guide device in an expanded configuration, in accordance with an embodiment of the present disclosure.

FIGS. 2A and 2B illustrate an embodiment of an expandable guide device of the present disclosure in an expanded configuration (FIG. 2A) and an unexpanded configuration (FIG. 2B). In this embodiment, two bodies 222a, 222b are present. A first device 220a is placed closer to a distal end 214 of the instrument 210. This first device 220a comprises the first body 222a which is substantially similar to that of FIG. 1C, with a compliant expandable member 240a disposed about the first body 222a, with a delivery member 250a in fluid communication with the expandable member 240a. A second device 220b is proximal to a proximal end 206 of the first device 220a. The second device 220b comprises a second body 222b with an expandable member 240b disposed about the second body 222b, with a delivery member 250b in fluid communication with the expandable member 240b. The expansion of each expandable member may be independent, due to the independent inflation fluid delivery members. The second body 222b may comprise a compliant expandable material. The first and second bodies 222a, 222b are configured such that an instrument 210 is extendible therethrough. The first body 222a resists deformation and may include a lubricious inner coating facing the instrument, allowing for translational and rotational movement of the instrument 210. The compliant second body 222b is able to compress onto the instrument 210 when the expandable member 240b is expanded. The compression against the instrument 210 axially fixes the instrument 210 in place with respect to the second body 222b. This embodiment allows the user to achieve the desired position of the instrument 210 within a body lumen by expanding the first expandable member 240a to prevent radial movement of the instrument 210 but allowing longitudinal and rotational movement with respect to the device. Once the instrument 210 is in place, the user may then expand the second expandable member 240b, which, due to the compliant body 222b and the compliant material of the expandable member 240b, expands both outwardly into the body lumen and inwardly onto the instrument 210, substantially locking instrument 210 in place. From this position, the instrument may be stabilized within the body lumen and procedures, for example access to the biliary papilla during an ERCP procedure, may be more easily performed.

FIG. 2C illustrates an embodiment with two devices 220a, 220b wherein the first device 220a extends distally, beyond the distal end of the instrument 310. The instrument 210 is still within the instrument lumen of the first body 222. The first body 222 is axially translated into this position by either translating the body 222 itself distal to the instrument 210 or axially translating the instrument 210 proximally from the body 222. When axially translating the instrument 210 proximally, the expandable member 240 of the device 220a is expanded, in order to maintain the body in position. When the expandable members 240, 241 are expanded, the body lumen is moved away from the instrument 210. This may improve the stability of the instrument and create a space between the instrument 210 and the body lumen, which creates more space in which the catheter 260 may be moved. In the embodiment of FIG. 2C, the arrangement of the expandable members on either side of the catheter 260 allows the user to stabilize the instrument on either side of the papilla, creating a stable, open space between the working channel of the instrument and the body lumen. The expansion of the expandable members could seal the area between the expandable members. When sealed, this area could be flooded with a fluid, which may improve ultrasound when used with an endoscopic ultrasound instrument or an ultrasound probe.

FIGS. 3A-3C illustrate an embodiment of an expandable guide device of the present disclosure, including an internal expandable member 360 disposed along an inward-facing surface of a body 322 of the expandable guide device and an external expandable member 340 disposed about an outward-facing surface of the body 322. The device is disposed at a distal end 314 of an instrument 310. The external expandable member 340 may be adhered to the outward-facing surface of the body 322. The internal expandable member 360 may be adhered to the inward-facing surface of the body 322. The internal expandable member may be disposed about the body and expandable radially from the inward-facing surface. The external expandable member may be disposed about the body and expandable radially from the outward-facing surface. FIG. 3A illustrates the device disposed about instrument 310 wherein the internal expandable member 360 and external expandable member 340 are partially expanded. A first delivery member 350 extends proximally from and in fluid communication with the external expandable member 340. A second delivery member 352 extends proximally from and in fluid communication with the internal expandable member 360. FIG. 3B illustrates a cross sectional view of the device wherein both the internal expandable member 360 and the external expandable member 340 are unexpanded about the instrument 310. FIG. 3C illustrates a cross sectional view of the device wherein both the internal expandable member 360 and the external expandable member 340 are expanded about the instrument 310. The internal expandable member 360, when expanded, fixes the instrument 310 within the body 322. This anchors the instrument 310 with respect to the device 304 and allows the user to translate the instrument 310 and device 304 simultaneously. The external expandable member 340 helps to anchor the device 304 with respect to the body lumen, pressing up against the walls of the body lumen. Similar to the previous embodiment, the external expandable member may stabilize the body lumen, and the instrument can continue to move within the body until properly positioned. Once positioned, the internal expandable member may be expanded, locking the instrument into place.

In various embodiments described herein and otherwise within the scope of the disclosure, frictional contact may be maintained between the internal expandable member and the instrument when the internal expandable member is expanded, allowing the device to move along with the instrument as the instrument is pushed or pulled through the body lumen. A stylet may also extend from a handle portion of the guide device, e.g., kept at the proximal end of the instrument, through an actuating member or delivery member of the device. The stylet can be used to push and/or pull the device in tandem with the instrument or relative to the instrument in order to position or reposition the device along and about the surface of the instrument. In order to move the device with the stylet, the internal expandable member is unexpanded. The stylet holds the device in place when only the instrument is moved relative to the device. When moving the device with the stylet relative to the instrument or moving the guide device and the instrument in tandem, the external expandable member can be expanded. The movement of the device along and about the instrument can be in a distal or proximal direction. Alternatively, the external expandable member may be expanded, the internal expandable member is not expanded, and the stylet is used to keep the device in place, allowing the instrument to move through the body lumen while the expanded external expandable member keeps the body lumen stabilized. An external expandable member may be expanded in order to contact the body lumen, partially expanded when the user is positioning the device and does not want to unexpand the expandable member, and unexpanded when moving the device through the body lumen. An internal expandable member may be expanded when moving the device with the instrument, partially expanded when the user is positioning the device, and unexpanded when moving the instrument or device separately. Each of these expanded, unexpanded, and partially expanded configurations may be used to position, stabilize, or otherwise assist the user in maneuvering the instrument within a body lumen.

In various embodiments herein or otherwise within the scope of the disclosure, the expandable members, both internal and external, may be annular around the body. The expandable members may be attached to the body at a single location and may not be circumferential about the body. An internal expandable member of this type may anchor the instrument within the body. An external expandable member of this type may anchor the body within the body lumen.

Figure 3D:
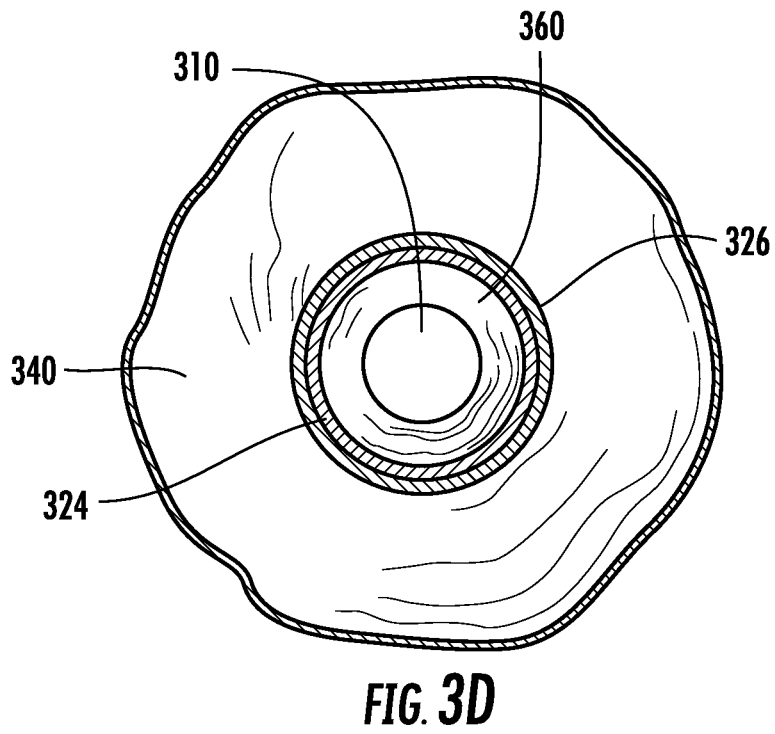
FIG. 3D illustrates a cross sectional view of an expandable guide device comprising two bodies, in accordance with an embodiment of the present disclosure.

FIG. 3D illustrates an embodiment of an expandable guide device of the present disclosure, including the internal expandable member 360 disposed along an inner surface of a first body 324, and the external expandable member 340 disposed about the outer surface of a second body 326. The device may be operated as described above. In FIG. 3D, both the internal expandable member 360 and the external expandable member 340 are expanded, such that the internal expandable member 360 is expanded about the instrument 310. A lubricious coating on the outer surface of the first body 324 and the inner surface of the second body 326 facilitates axial and rotational movement of the first body 324 within the second body 326. When in this configuration, the external expandable member 340 is expanded into a body lumen, stabilizing the body lumen. The internal expandable member 360 is expanded onto the instrument 310, stabilizing the instrument 310 within the body lumen. The instrument 310 may still be moved axially and rotationally with the first body 324, allowing the user to position the instrument 310 while stabilizing the body lumen.

Figure 3E:
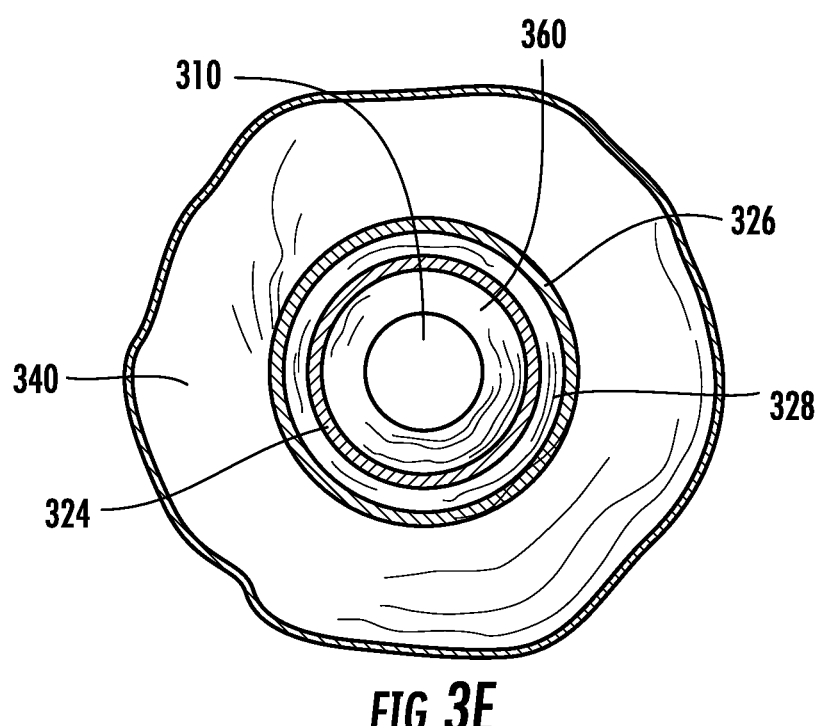
FIG. 3E illustrates a cross sectional view of an expandable guide device comprising a central expandable member, in accordance with an embodiment of the present disclosure.

FIG. 3E illustrates an embodiment of an expandable guide device of the present disclosure, including the internal expandable member 360 disposed along an inner surface of the first body 324, and the external expandable member 340 disposed about the outer surface of the second body 326. The device may be operated as described above. A central expandable member 328 is disposed between the outer surface of the first body 324 and the inner surface of the second body 326. The central expandable member 328 may be adhered to either the first body 324 or the second body 326. When the internal expandable member 360 is expanded, the instrument 310 cannot move axially but the device can rotate with the instrument 310. When the central expandable member 328 is expanded, the first body 324 and second body 326 are prevented from rotating. The central expandable member 328 may be circumferential, e.g., annular balloon as shown in FIG. 3E. Alternatively, the central expandable member 328 may extend along only a portion of the circumference, and/or extend along only a portion of the axial length, of the first or second body. If central expandable member 328 is only partially circumferential, then more than one member 328 may be uniformly or non-uniformly arranged and space around the circumference of the first body or the second body.

Figure 3F:
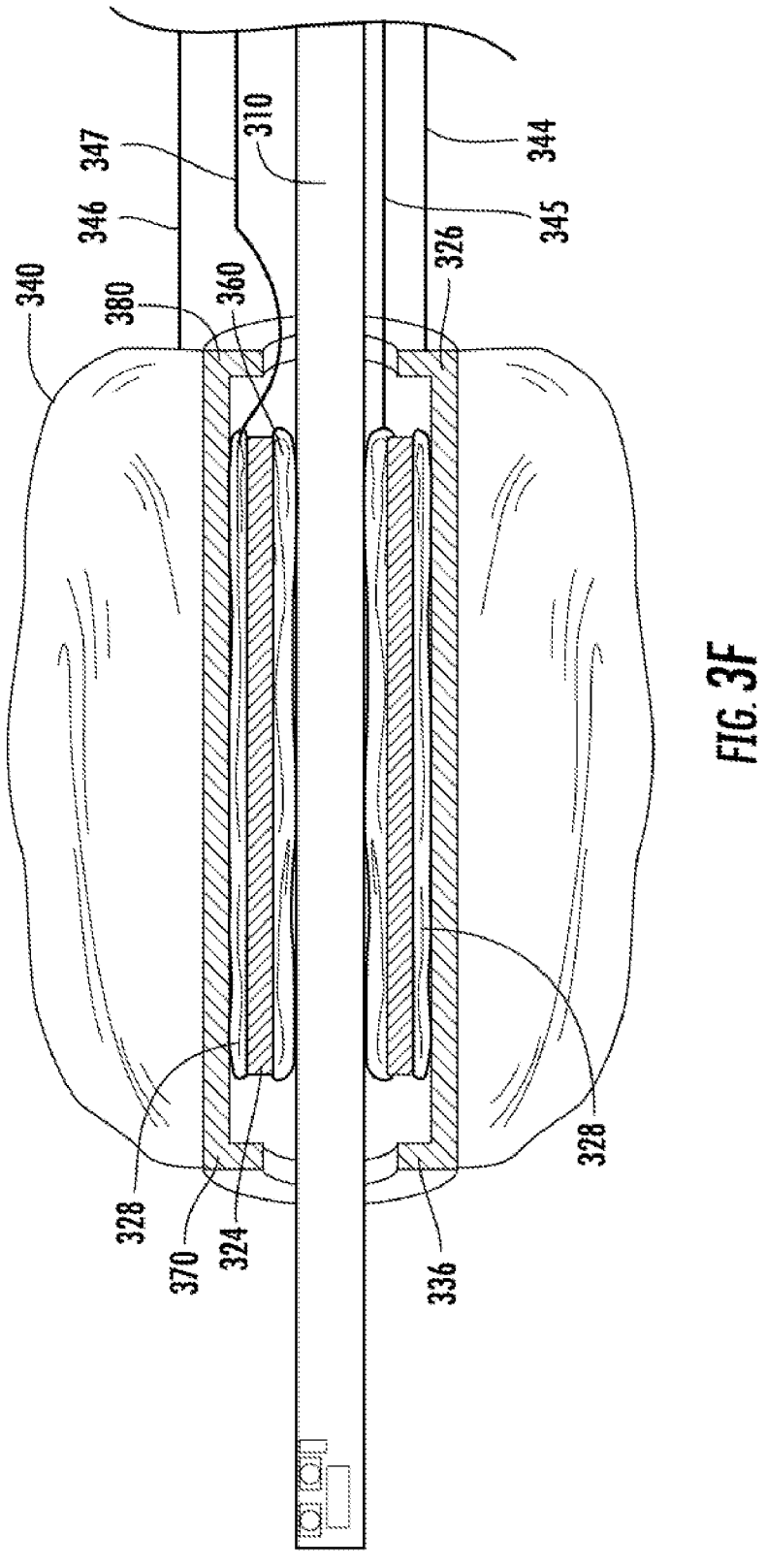
FIG. 3F illustrates a cross sectional view of an expandable guide device in an expanded configuration, in accordance with an embodiment of the present disclosure.

FIG. 3F illustrates an embodiment of an expandable guide device of the present disclosure. The device may be operated to allow for axial and rotational movement of the instrument and the bodies with expandable members, both among each other and individually or collectively with respect to the body lumen, as described above. In this embodiment, the device includes the internal expandable member 360 disposed about the inner surface of the first body 324 and in fluid communication with an internal expandable member delivery member 345. The external expandable member 340 is disposed about the outer surface of the second body 326 and in fluid communication with the external expandable member delivery member 346. The central expandable member 328 is disposed between the first body 324 and the second body 326 and in fluid communication with the central expandable member delivery member 347. The expansion of each expandable member may be independent, due to the independent inflation fluid delivery members. The central expandable member 347 may be configured as described above with respect to FIG. 3E, as an annular member, or as a partially circumferential members(s). The second body 326 has a greater length than the first body 324 and has flanges 336 extending from the distal end 370 and proximal end 380 of the second body 326. The difference in length between the first body 324 and the second body 326 allow the first body 324 to move axially if the center expandable member 328 is not expanded. The flanges 336 prevent the first body 324 from moving axially beyond the second body 326. The first body 324 may be moved axially within the second body when the internal expandable member 360 is expanded, gripping the instrument 310, and the instrument 310 is moved axially while the second body 326 is held in place with a delivery member 344. Other examples of manipulating the device and instrument with respect to each other, and/or individually or together with respect to the body lumen, are contemplated.

FIG. 3G an embodiment of an expandable guide device of the present disclosure. The device may be operated to allow for axial and rotational movement of the instrument and the bodies with expandable members, both among each other and individually or collectively with respect to the body lumen, as described above. The device includes the internal expandable member 360 disposed about an inner surface of the first body 324, and the external expandable member 340 disposed about the outer surface of the second body 326. The second body 326 contains a protrusion 332 along the inner surface of the body 326, which is matched by a notch 334 in the outer surface of the first body 324. As the notch 334 and protrusion 332 are interlocked, the first body 324 and second body 326 may be moved axially with respect to one another, but may not rotate about each other. The notch 334 extends from the proximal end of the first body to the distal end, creating a groove along which the protrusion 332 (which extends from the proximal end of the second body to the distal end) may slide. At the distal and proximal ends of the second body 326, there may be a flange which stops the first body 324 from sliding out from within the second body 326. This allows the first body 324 and second body 326 to move axially. Additionally, or alternatively, a central expandable member 330 may be incorporated as an axial brake between the first and second body. When the central expandable member 330 is expanded, the first body 324 and second body 326 may not move slide axially with respect to one another. Respective internal, external and central expandable members, 360, 340, 330, may be in fluid communication with independent corresponding internal, external, and central expandable member delivery members 345, 346, 347 (not shown), similar to the device of FIG. 3F.

In various embodiments herein or otherwise within the scope of the disclosure, a plurality of expandable members may be used to facilitate movement, stabilize, and/or position an instrument. For example, as seen in FIG. 3G, the internal expandable member 360 is expanded by the internal expandable member delivery member 345. When only the internal expandable member 360 is expanded, the instrument 310 and the first body 324 may be moved axially within the second body 326, and the instrument 310, the first body 324, and the second body 326 may be moved rotationally within a body lumen. When the internal expandable member 360 and the center expandable member 330 are expanded, the first body 324 and second body 326 move axially and rotationally with the instrument 310. When the internal expandable member 360, center expandable member 330, and external expandable member 340 are expanded, the instrument 310, first body 324, and second body 326 are all locked in place, stabilizing the instrument within the body lumen.

In various embodiments described herein or otherwise within the scope of the disclosure, a plurality of bodies having expandable members may be used with a single instrument, as seen in FIGS. 3A-3G, and 4A-4B. Because the placement of the device on the instrument can provide for variations in use, it may be beneficial to have more than one body along the instrument. Further, the use of an expandable guide device with a first body (e.g., the first body 220a of FIG. 2A) along with a second body (e.g., the second body 220b of FIG. 2A) facilitates various positioning or restrictions on movement of the bodies to be made along various lengths of the instrument, either individually or simultaneously. For example, the embodiment of FIG. 2A facilitates the inflation of the distal body 220a, which facilitates continued longitudinal and axial movement with respect to the device, and then the inflation of the proximal body 220b, which will substantially inhibit movement of the instrument 210 within the body lumen. The expandable guide devices may be strategically located along the instrument, and with respect to each other, to provide, e.g., steering capability that is not readily achievable with the instrument not having the devices, such as locating along a colonoscope at a position that is helpful to navigate tortuous anatomy without creating undesired loops in the endoscope.

Figure 4A:
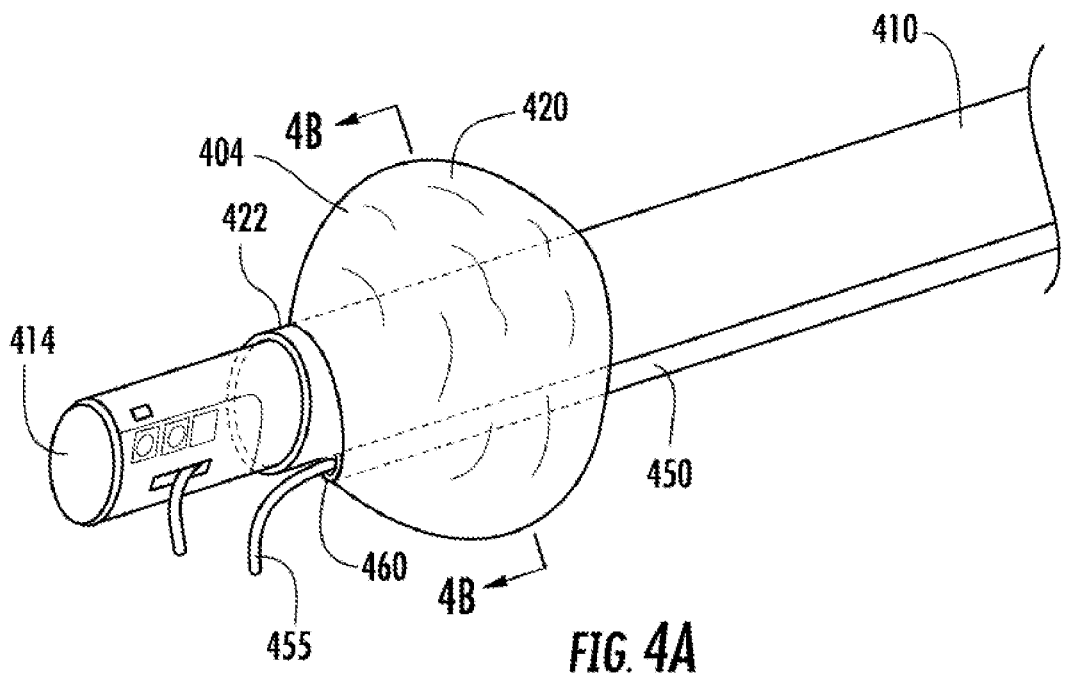
FIG. 4A illustrates a perspective view of an expandable guide device in an expanded configuration, in accordance with an embodiment of the present disclosure.
Figure 4B:
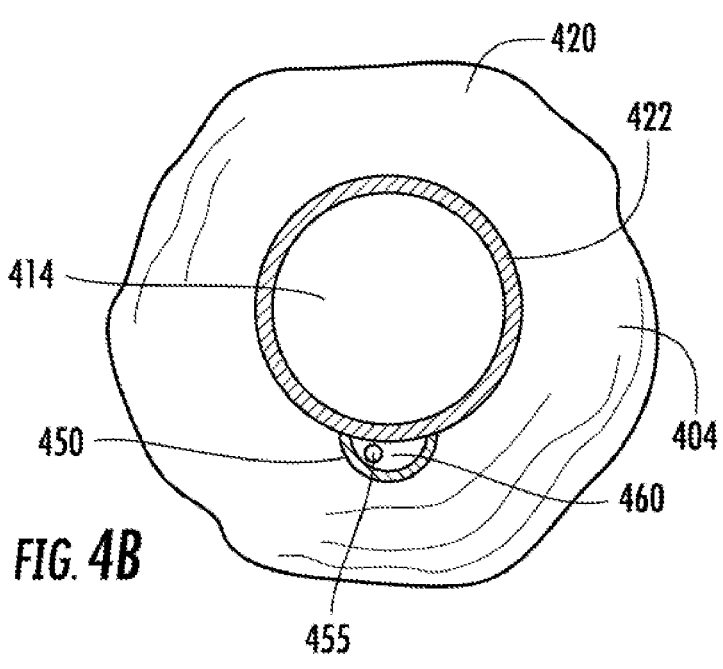
FIG. 4B illustrates a cross sectional view of the device of FIG. 4A.

FIGS. 4A-B illustrate an embodiment of the present disclosure in which the expandable guide device includes an elongate member 410 including a portion 450 having a lumen 460. The device may be operated as described above. A secondary instrument 455 may be slidably moved through the lumen 460 of the elongate member 450 for use within the body lumen. FIG. 4B depicts a cross sectional view of this embodiment. The elongate member 460 extends along an outer wall of the body 422, with the expandable member 420 disposed about both the body 422 and the elongate member 450. This configuration allows the secondary instrument 455 to be translated through the body lumen and distal to a stabilized device 404 in order to reach a desired portion of the body lumen. This secondary instrument may be used in conjunction with a first tool inserted through the first instrument, e.g., through the working channel of an endoscope 414. The visualization capabilities of the endoscope, the stability and positioning capabilities of the endoscope 414 provided by the accessory device(s), as a platform from which to work with two or more tools provide a useful endo-surgical system.

Figure 5A:
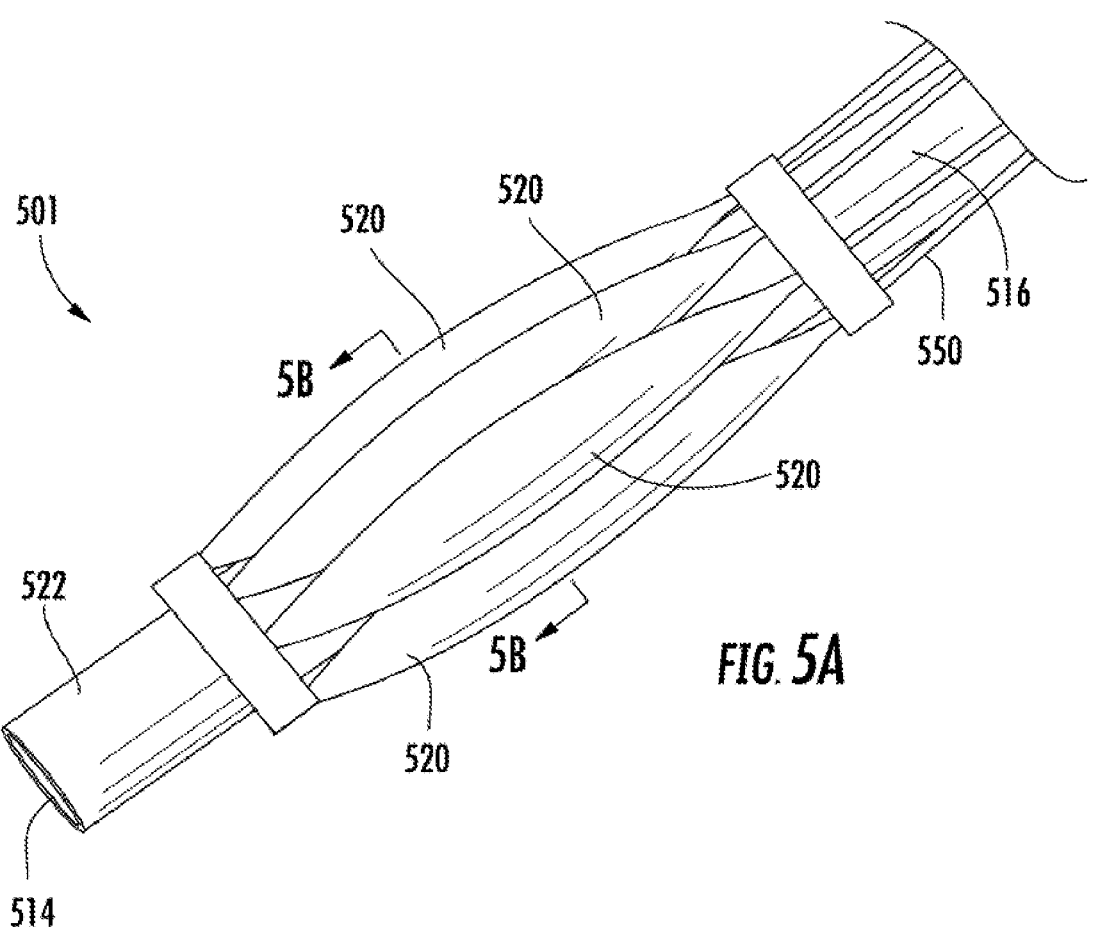
FIG. 5A illustrates a perspective view of an expandable guide device in an expanded configuration, in accordance with an embodiment of the present disclosure.
Figure 5B:
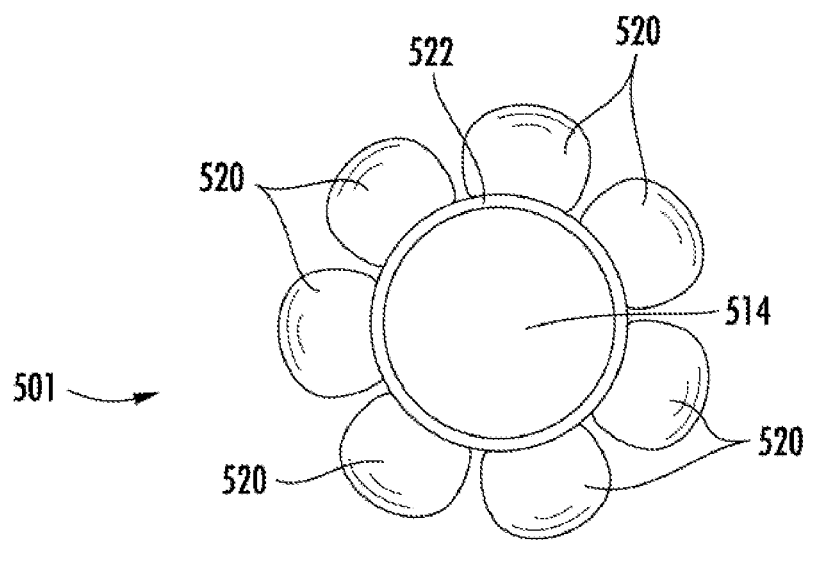
FIG. 5B illustrates a cross-sectional view of the expandable guide device of FIG. 5A in a partially unexpanded configuration.
Figure 5C:
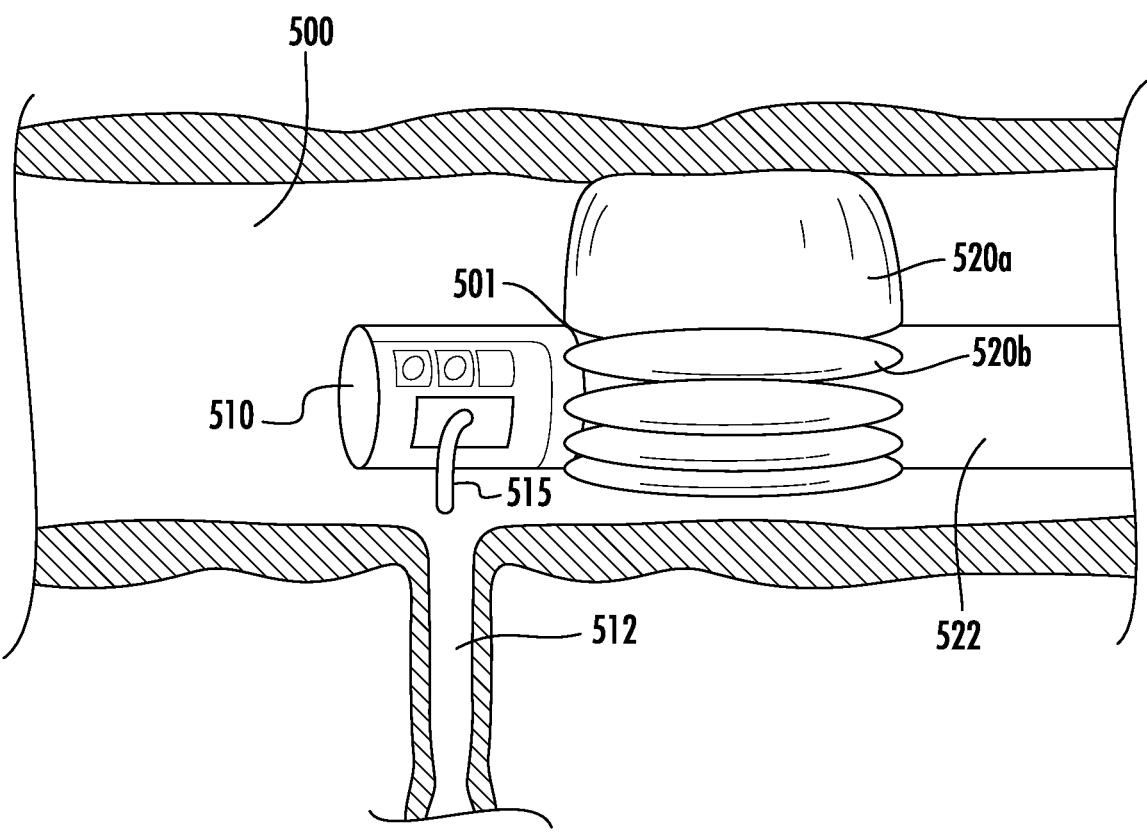
FIG. 5C illustrates a side view of the expandable guide device of FIGS. 5A and 5B, with expandable members in various statues of expansion, in accordance with an embodiment of the present disclosure.

FIGS. 5A-5C illustrate an embodiment of an expandable guide device 501 of the present disclosure, including a plurality of expandable members 520. The device 501 may be similarly operated as described above with other embodiments. The expandable members 520 are disposed about the circumference of a body 522 having a lumen 514. Each expandable member 520 includes a delivery member 550 extending proximally along the body 522, with the distal end of the body 522 toward the distal end of the instrument. FIG. 5B illustrates a cross sectional view of expandable guide device of FIG. 5A with the body 522 and the expandable members 520. In this configuration, the plurality of expandable members 520 can be expanded independently, causing the body 522 to move radially or laterally in the body lumen in a direction opposing the expansion. FIG. 5C illustrates an example of the expandable guide device 501 disposed about an instrument 510 within a body lumen 500. In order to radially translate the instrument 510 toward the papilla 512 within the body lumen 500, an expandable member 520a may be expanded, pushing against the body lumen 500, while the remaining expandable members 520b are unexpanded/partially expanded. This allows the instrument 510 to be radially offset within the body lumen 500 in any number of radial locations within the body lumen 500 by independently and selectively expanding the members to varying degrees of expansion, as dictated by the desired location of the instrument within the body lumen. This may also be desired for purposes of establishing a certain angle of approach to the papilla. Members 520 may be partially or fully expanded in various combination to move the instrument 510 in any radial direction.

In various embodiments described herein or otherwise within the scope of the disclosure, the distal end of the instrument may or may not extend past the distal end of the expandable guide device.

In various embodiments described herein or otherwise within the scope of the disclosure, the device may comprise a sensor.

In various embodiments described herein or otherwise within the scope of the disclosure, a central axis of the first body may be offset from a central axis of the first expandable member when the first expandable member is in an expanded configuration.

In various embodiments described herein or otherwise within the scope of the disclosure, an expandable member may expand to a greater or lesser degree than a different expandable member.

In various embodiments described herein or otherwise within the scope of the disclosure, the expandable guide device may be disposable. In alternate embodiments, the expandable guide device may be reusable.

In various embodiments described herein or otherwise within the scope of the disclosure, a method of performing an endoscopy may include coupling at least one expandable guide device with an instrument. The device may include a first expandable member and a second expandable member. The instrument and the at least one expandable guide device are together inserted into a body lumen. The instrument and device may be advanced toward a treatment site. The expandable member may be expanded within the body lumen, contacting and even to some degree dilating the patient's body lumen, e.g., the duodenum, the intestines, or the like. The expandable guide device increases in diameter when the expandable member is expanded, inhibiting radial, longitudinal, and/or axial movement of both the instrument and the expandable guide device. The method may comprise expanding the second expandable member to provide lateral stabilization of the instrument with respect to the body lumen. Expanding the expandable member allows the instrument to remain stable while using the instrument to examine other areas of the body. This can occur due to the outer diameter of the expandable member contacting or dilating the body lumen, inhibiting or preventing movement of the device, as well as through selective expansion of expandable members to position the instrument.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. An expandable guide device, comprising:

a first body having a proximal end, a distal end, an inner surface, an outer surface, and a first body lumen extending therethrough along a longitudinal axis;

an internal expandable member disposed along an inner surface of the first body and expandable inwardly from the inner surface of the first body onto an instrument disposed within the first body lumen, the internal expandable member attached to the inner surface of the first body;

a second body having a proximal end, a distal end, an inner surface, an outer surface, and a second body lumen extending therethrough along a longitudinal axis, the first body disposed within the second body lumen;

an external expandable member disposed about the outer surface of the second body and expandable outwardly from the outer surface of the first body, the external expandable member attached to the outer surface of the second body; and a central expandable member disposed between the outer surface of the first body and the inner surface of the second body, the central expandable member attached to either the first body or the second body;

wherein (a) the second body has a length that is greater than a length of the first body and the second body has flanges that extend radially inward from the distal and proximal ends of the second body or (b) the central expandable member extends along only a portion of a circumference of the first body.

2. The device of claim 1, wherein the external expandable member comprises a compliant material.

3. The device of claim 1, further comprising at least one delivery member in fluid communication with at least one of the external expandable member, the central expandable member and the internal expandable member.

4. The device of claim 1, wherein the external expandable member further comprises a sensor.

5. The device of claim 1, wherein a central axis of the second body is offset from a central axis of the external expandable member when the external expandable member is in an expanded configuration.

6. The device of claim 3, wherein the at least one delivery member is in fluid communication with the external expandable member the central expandable member and the internal expandable member.

7. The device of claim 1, further comprising an elongate member disposed along an outer surface of the second body, the elongate member comprising a lumen extending therethrough.

8. The device of claim 3, wherein the at least one delivery member is in fluid communication with a supply of $CO_2$, contrast fluid, or air.

9. The device of claim 1, wherein the external expandable member, or the internal expandable member, or both, are spherical-shaped, oblong-shaped, or ellipsoidal-shaped.

10. A system, comprising:

an instrument; and the expandable guide device of claim 1 slidably disposed about the instrument.

11. A method, comprising:

coupling the expandable guide device of claim 1 with an instrument;

inserting the instrument and device into a body lumen;

advancing the instrument and device toward a treatment site; and expanding the external expandable member against a wall of the body lumen.

12. The method of claim 11, wherein expanding the external expandable member facilitates longitudinal and rotational movement of the instrument relative to the expandable guide device.

13. The method of claim 11, further comprising expanding the internal expandable member to provide lateral stabilization of the instrument with respect to the body lumen.

14. The method of claim 11, wherein the external expandable member is expanded to place the instrument in position to interact with the treatment site, and the internal expandable member is expanded to laterally stabilize the instrument with respect to the body lumen.

15. The device of claim 1, wherein the length of the second body is greater than the length of the first body and the second body has flanges that extend radially inward from the distal and proximal ends of the second body.

16. The device of claim 1, wherein the central expandable member extends along only the portion of the circumference of the first body.

17. The device of claim 16, wherein the second body contains a protrusion along the inner surface of the second body, which is matched by a notch in the outer surface of the first body.

18. The device of claim 17, wherein the notch extends along a length of the first body, forming a groove along which the protrusion may slide.

\* \* \* \* \*